(12) United States Patent
Smith

(10) Patent No.: US 11,872,385 B2
(45) Date of Patent: Jan. 16, 2024

(54) BLOOD PUMP WITH MAGNETICALLY LOADED PARTIAL ARC JOURNAL BEARING

(71) Applicant: THE CLEVELAND CLINIC FOUNDATION, Cleveland, OH (US)

(72) Inventor: William Smith, Cleveland, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 418 days.

(21) Appl. No.: 16/980,795

(22) PCT Filed: Mar. 13, 2019

(86) PCT No.: PCT/US2019/021964
§ 371 (c)(1),
(2) Date: Sep. 14, 2020

(87) PCT Pub. No.: WO2019/178173
PCT Pub. Date: Sep. 19, 2019

(65) Prior Publication Data
US 2021/0085954 A1    Mar. 25, 2021

Related U.S. Application Data

(60) Provisional application No. 62/642,756, filed on Mar. 14, 2018.

(51) Int. Cl.
*A61M 1/00* (2006.01)
*A61M 60/82* (2021.01)
(Continued)

(52) U.S. Cl.
CPC .......... *A61M 60/82* (2021.01); *A61M 60/148* (2021.01); *A61M 60/178* (2021.01);
(Continued)

(58) Field of Classification Search
CPC ... A61M 60/422; A61M 60/825; A61M 60/82
See application file for complete search history.

(56) References Cited

U.S. PATENT DOCUMENTS 5,507,629 A   4/1996 Jarvik
5,749,855 A   5/1998 Reitan
(Continued)

FOREIGN PATENT DOCUMENTS

EP    2438937 A1    4/2012
WO    1997/37696 A1    10/1997
(Continued)

OTHER PUBLICATIONS

PCT International Search Report and Written Opinion for corresponding International Application Serial No. PCT/US2019/021964, dated Sep. 2, 2019, pp. 1-19.
(Continued)

*Primary Examiner* — Michael J D'Abreu
(74) *Attorney, Agent, or Firm* — TAROLLI, SUNDHEIM, COVELL & TUMMINO L.L.P.

(57) ABSTRACT

A blood pump (10) includes a pump housing (30) having a pump inlet (16) and a pump outlet (18) spaced apart along a longitudinally extending central pump axis (28). The blood pump (10) also includes a rotating assembly (100) comprising an impeller (104). The blood pump (10) further includes partial arc journal bearings (160, 180) that support the rotating assembly (100) for rotation in the housing (30). The rotating assembly (100) is rotatable relative to the housing (30) to pump blood from the pump inlet (16) to the pump outlet (18).

69 Claims, 7 Drawing Sheets

Figure 3:
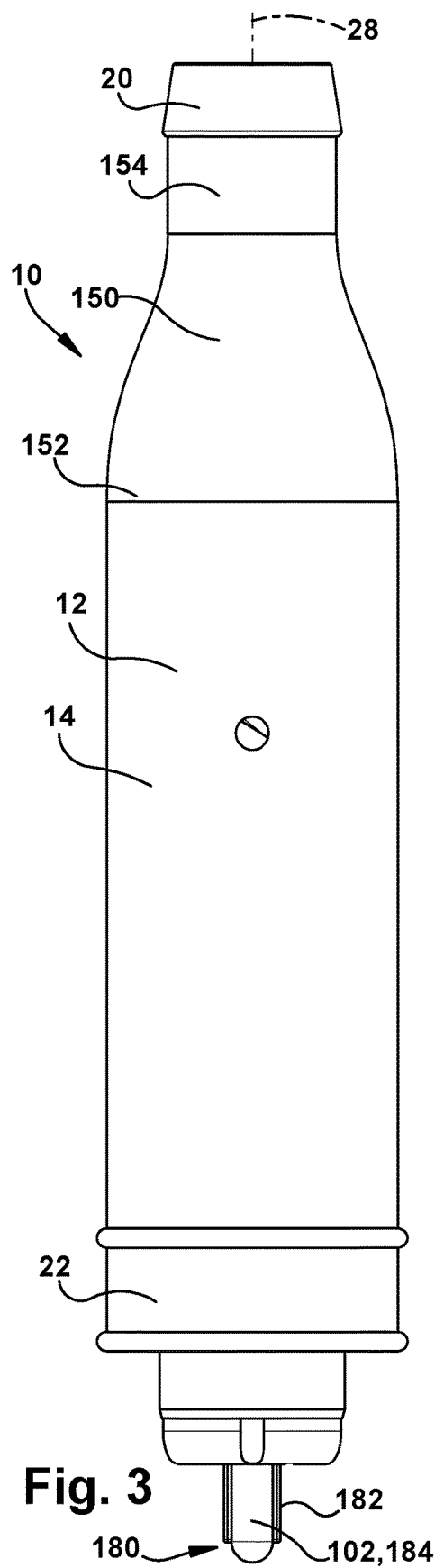

(51) Int. Cl.
    *A61M 60/824* (2021.01)
    *A61M 60/148* (2021.01)
    *A61M 60/178* (2021.01)
    *A61M 60/825* (2021.01)
    *A61M 60/812* (2021.01)
    *A61M 60/422* (2021.01)
    *A61M 60/237* (2021.01)

(52) U.S. Cl.
    CPC ........ *A61M 60/237* (2021.01); *A61M 60/422* (2021.01); *A61M 60/812* (2021.01); *A61M 60/824* (2021.01); *A61M 60/825* (2021.01); *A61M 2205/103* (2013.01); *A61M 2210/125* (2013.01)

(56) References Cited

U.S. PATENT DOCUMENTS

| | | | |
|---|---|---|---|
| 6,080,133 | A | 6/2000 | Wampler |
| 6,093,001 | A * | 7/2000 | Burgreen ............ F04D 29/0413 415/176 |
| 2008/0269880 | A1 | 10/2008 | Jarvik |
| 2009/0259308 | A1 * | 10/2009 | Hidaka ................ A61M 60/82 623/3.13 |
| 2011/0236187 | A1 * | 9/2011 | Jarvik .................... F16C 17/08 384/100 |

FOREIGN PATENT DOCUMENTS

| | | |
|---|---|---|
| WO | 1997/37697 A1 | 10/1997 |
| WO | 1997/37698 A1 | 10/1997 |
| WO | 2005/030296 A2 | 4/2005 |

OTHER PUBLICATIONS

Duncan, Brian W.*; Dudzinski, David T.†; Gu, Lei†; Mielke, Nicole†; Noecker, Angela M.†; Kopcak, Michael W.†; Fukamachi, Kiyotaka†; Cingoz, Faruk†; Ootaki, Yoshio†; Smith, William A.† The PediPump: Development Status of a New Pediatric Ventricular Assist Device: Update II, ASAIO Journal: Sep. 2006—vol. 52—Issue 5—p. 581-587 doi: 10.1097/01.mat.0000235821.63492.c4.

Duncan, Brian W.*; Dudzinski, David T.†; Noecker, Angela M.†; Kopcak, Michael W.†; Fukamachi, Kiyotaka†; Ootaki, Yoshio†; Chen, H Ming‡; Chapman, Peter A.‡; Smith, William A.† The PediPump: Development Status of a New Pediatric Ventricular Assist Device, ASAIO Journal: Sep.-Oct. 2005—vol. 51—Issue 5—p. 536-539 doi: 10.1097/01.mat.0000178211.70743.99.

Duncan, Brian W., et al. "The PediPump: a new ventricular assist device for children." Artificial organs 29.7 (2005): 527-530.

Wilhelm, M. J., et al. "Clinical experience with nine patients supported by the continuous flow Debakey VAD." The Journal of Heart and Lung Transplantation 20.2 (2001): 201.

Rothenburger, Markus, et al. "Treatment of thrombus formation associated with the MicroMed DeBakey VAD using recombinant tissue plasminogen activator." Circulation 106.12_suppl_1 (2002): I-189.

Delgado, Reynolds, and Marianne Bergheim. "HeartMate® II left ventricular assist device: a new device for advanced heart failure." Expert review of medical devices 2.5 (2005): 529-532.

Esmore, Donald S., et al. "First clinical implant of the VentrAssist left ventricular assist system as destination therapy for end-stage heart failure." The Journal of heart and lung transplantation 24.8 (2005): 1150-1154.

Griffith, Bartley P., et al. "HeartMate II left ventricular assist system: from concept to first clinical use." The Annals of thoracic surgery 71.3 (2001): S116-S120.

Ochiai, Yoshie; Golding, Leonard A.R.; Massiello, Alex L.; Medvedev, Alexander L.; Horvath, David J.; Gerhart, Renee L.; Chen, Ji-Feng; Krogulecki, Alexandra Y.; Takagaki, Masami; Doi, Kazuyoshi; Howard, Michael W.; Fukamachi, Kiyotaka Cleveland Clinic CorAide Blood Pump Circulatory Support Without Anticoagulation, ASAIO Journal: May-Jun. 2002—vol. 48—Issue 3—p. 249-252.

Sweeney, Michael S. "The Hemopump in 1997: a clinical, political, and marketing evolution." The Annals of thoracic surgery 68.2 (1999): 761-763.

Garatti, Andrea, et al. "Different applications for left ventricular mechanical support with the Impella Recover 100 microaxial blood pump." The Journal of heart and lung transplantation 24.4 (2005): 481-485.

Siess, Thorsten, Christoph Nix, and Frank Menzler. "From a lab type to a product: a retrospective view on Impella's assist technology." Artificial organs 25.5 (2001): 414-421.

Garatti, A., et al. "Impella recover 100 microaxial left ventricular assist device: the Niguarda experience." Transplantation proceedings. vol. 36. No. 3. Elsevier, 2004.

Schmid, Christof, et al. "First clinical experience with the Incor left ventricular assist device." The Journal of heart and lung transplantation 24.9 (2005): 1188-1194.

Takatani, Setsuo, et al. "Mechanical circulatory support devices (MCSD) in Japan: current status and future directions." Journal of Artificial Organs 8.1 (2005): 13-27.

De Robertis, Fabio, et al. "Clinical performance with the Levitronix Centrimag short-term ventricular assist device." The Journal of heart and lung transplantation 25.2 (2006): 181-186.

Chen, H Ming*; Smith, William A.†; Walton, James F.* High Efficiency Magnetic Bearing for a Rotary Blood Pump, ASAIO Journal: Sep. 1998—vol. 44—Issue 5—p. M728-M732.

Baldwin, J. Timothy, et al. "The national heart, lung, and blood institute pediatric circulatory support program." Circulation 113.1 (2006): 147-155.

Jikuya, Tomoaki, et al. "Development of an atraumatic small centrifugal pump for second-generation cardiopulmonary bypass." Artificial organs 16.6 (1992): 599-606.

Oku, Takahiko; Harasaki, Hiroaki; Smith, William; Nosé, Yukihiko A Comparative Study of Four Nonpulsatile Pumps, ASAIO Transactions: Jul. 1988—vol. 34—Issue 3—p. 500-504.

Tanaka, S., Yamamoto, S., Yamakoshi, K., and Kamiya, A. (Aug. 1, 1987). "A Compact Centrifugal Blood Pump for Extracorporeal Circulation: Design and Performance." ASME. J Biomech Eng. Aug. 1987; 109(3): 272-278. https://doi.org/10.1115/1.3138680.

Jakob, Heinz, et al. "In-vitro assessment of centrifugal pumps for ventricular assist." Artificial organs 14.4 (1990): 278-283.

Burton, Alan C. Physiology and Biophysics of the Circulation, Journal of Medical Education: Aug. 1965—vol. 40—Issue 8—p. xxx-xxxvi.

Carter, Janell; Hristova, Katia; Harasaki, Hiroaki; Smith, W. A. Short Exposure Time Sensitivity of White Cells to Shear Stress, ASAIO Journal: Nov. 2003—vol. 49—Issue 6—p. 687-691 doi: 10.1097/01.MAT.0000094194.93742.A7.

Casas, Fernando*; Reeves, Andrew*; Dudzinski, David*; Weber, Stephan*; Lorenz, Markus*; Akiyama, Masatoshi*; Kamohara, Keiji*; Kopcak, Michael*; Ootaki, Yoshio*; Zahr, Firas*; Sinkewich, Martin†; Foster, Robert†; Fukamachi, Kiyotaka*; Smith, William A.* Performance and Reliability of the CPB/ECMO Initiative Forward Lines Casualty Management System, ASAIO Journal: Nov.-Dec. 2005—vol. 51—Issue 6—p. 681-685 doi: 10.1097/01.mat.0000182472.63808.b9.

Golding, Leonard, et al. "Cleveland clinic continuous flow blood pump: Progress in development." (1998): 447-450.

Gu, Lei; Smith, William A. Evaluation of Computational Models for Hemolysis Estimation, ASAIO Journal: May-Jun. 2005—vol. 51—Issue 3—p. 202-207 doi: 10.1097/01.MAT.0000161939.29905.93.

Gu, Lei*; Smith, William A.*; Chatzimavroudis, George P.† Mechanical Fragility Calibration of Red Blood Cells, ASAIO Journal: May-Jun. 2005—vol. 51—Issue 3—p. 194-201 doi: 10.1097/01.MAT.0000161940.30190.6D.

Lorenz, Markus, and William A. Smith. "Rotodynamic pump scaling." Asaio Journal 48.4 (2002): 419-430.

Schenk, Soren*; Weber, Stephan*; Luangphakdy, Viviane*; Flick, Christine R.*; Chen, Ji-Feng*; Inoue, Masahiro*; Kopcak, Michael W. Jr.*; Ootaki, Yoshio*; Doi, Kazuyoshi*; Dessoffy, Raymond*; Hirschman, Gordon B.†; Vitale, Nicholas G.†; Chapman, Peter A. Jr.†; Smith, William A.*; Fukamachi, Kiyotaka* In Vivo Perfor-

(56) References Cited

OTHER PUBLICATIONS mance and Biocompatibility of the MagScrew Ventricular Assist Device, ASAIO Journal: Sep.-Oct. 2003—vol. 49—Issue 5—p. 594-598.

Schenk, Soren, et al. "MagScrew total artificial heart in vivo performance above 200 beats per minute." The Annals of thoracic surgery 79.4 (2005): 1378-1383.

Smith, W. A.*; Allaire, P.†; Antaki, J.‡; Butler, K. C.§; Kerkhoffs, W.¶; Kink, T.*; Loree, H.?; Reul, H.¶ Collected Nondimensional Performance of Rotary Dynamic Blood Pumps, ASAIO Journal: Jan.-Feb. 2004—vol. 50—Issue 1—p. 25-32 doi: 10.1097/01.MAT. 0000104817.39941.9C.

Veres, Joseph P., et al. "Flow analysis of the Cleveland Clinic centrifugal pump." (1997).

Weber, Stephan*; Kamohara, Keiji*; Klatte, Ryan S.*; Luangphakdy, Viviane*; Flick, Christine*; Chen, Ji-Feng*; Casas, Fernando*; Ootaki, Yoshio*; Kopcak, Michael*; Akiyama, Masatoshi*; Hirschman, Gordon B.†; Chapman, Peter A.†; Donahue, Arthur†; Wetterau, William†; Prisco, Charles†; Mast, Roy‡; Sherman, Craig§; Fukamachi, Kiyotaka*; Smith, William A.* MagScrew TAH: An Update, ASAIO Journal: Nov.-Dec. 2005—vol. 51—Issue 6—p. xxxvi-xlvi.

Malanoski, Stanley B., et al. "Stable blood lubricated hydrodynamic journal bearing with magnetic loading." ASAIO Journal (American Society for Artificial Internal Organs: 1992) 44.5 (1998): M737-40.

Murray, S. Frank, et al. "Selection and evaluation of blood-and tribologically compatible journal bearing materials." ASAIO Journal (American Society for Artificial Internal Organs: 1992) 43.5 (1997): M603-8. Abstract Only.

Walowit JA, Malanoski SB, Horvath D, Golding LR, Smith WA. The analysis, design, and testing of a blood lubricated hydrodynamic journal bearing. ASAIO Journal (American Society for Artificial Internal Organs : 1992). Sep.-Oct. 1997;43(5):M556-9. Abstract Only.

Xu, Longya, et al. "Analysis of a new PM motor design for a rotary dynamic blood Pump." ASAIO Journal (American Society for Artificial Internal Organs: 1992) 43.5 (1997): M559-64. Abstract Only.

Sankovic, John M., et al. "PIV investigations of the flow field in the volute of a rotary blood pump." J. Fluids Eng. 126.5 (2004): 730-734.

Benincasa, Maria-Anna, et al. "Cell sorting by one gravity SPLITT fractionation." Analytical chemistry 77.16 (2005): 5294-5301.

Lara, Oscar, et al. "Enrichment of rare cancer cells through depletion of normal cells using density and flow-through, immunomagnetic cell separation." Experimental hematology 32.10 (2004): 891-904.

McCloskey, Kara E., Jeffrey J. Chalmers, and Maciej Zborowski. "Magnetic cell separation: characterization of magnetophoretic mobility." Analytical chemistry 75.24 (2003): 6868-6874.

Moore, Lee R., et al. "Control of magnetophoretic mobility by susceptibility-modified solutions as evaluated by cell tracking velocimetry and continuous magnetic sorting." Analytical chemistry 76.14 (2004): 3899-3907.

Williams, P. Stephen, et al. "Splitter imperfections in annular split-flow thin separation channels: effect on nonspecific crossover." Analytical chemistry 75.6 (2003): 1365-1373.

Zborowski, Maciej, and Jeffrey J. Chalmers. "Magnetic cell sorting." Immunochemical Protocols. Humana Press, 2005. 291-300.

Carpino, Francesca, et al. "Quadrupole magnetic field-flow fractionation for the analysis of magnetic nanoparticles." Journal of Physics: Conference Series. vol. 17. No. 1. IOP Publishing, 2005.

* cited by examiner

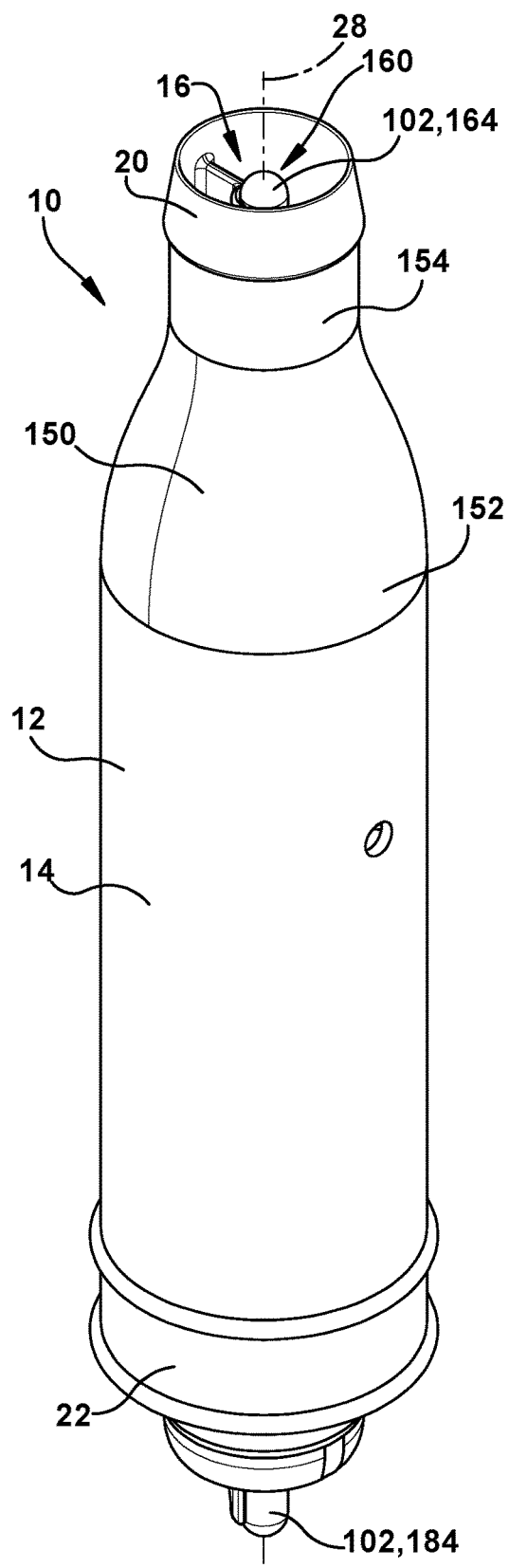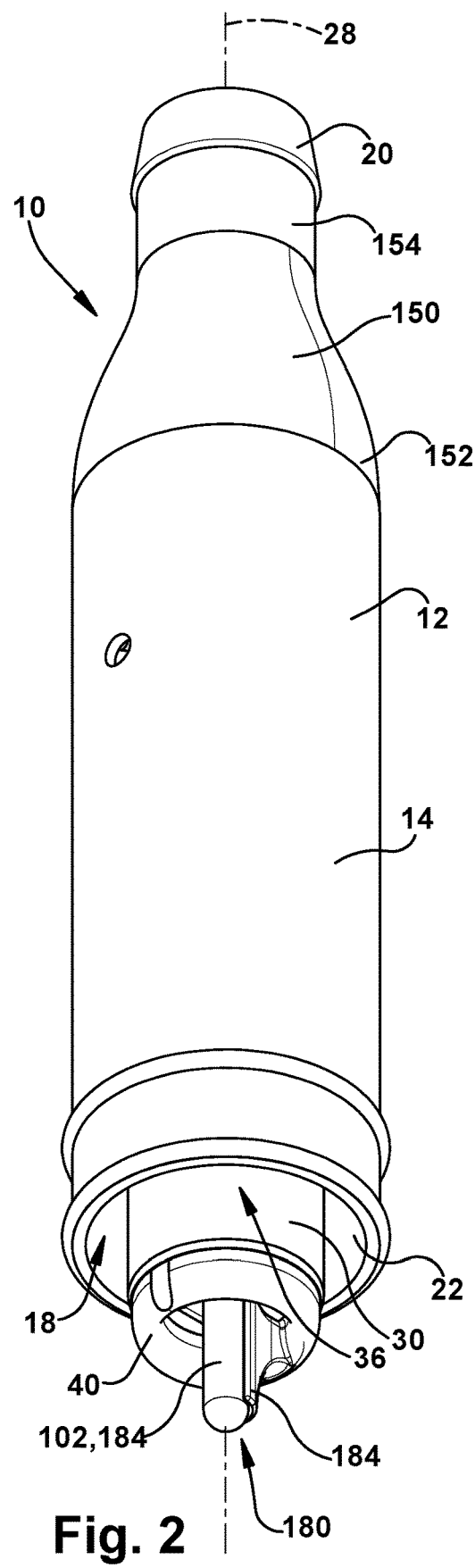

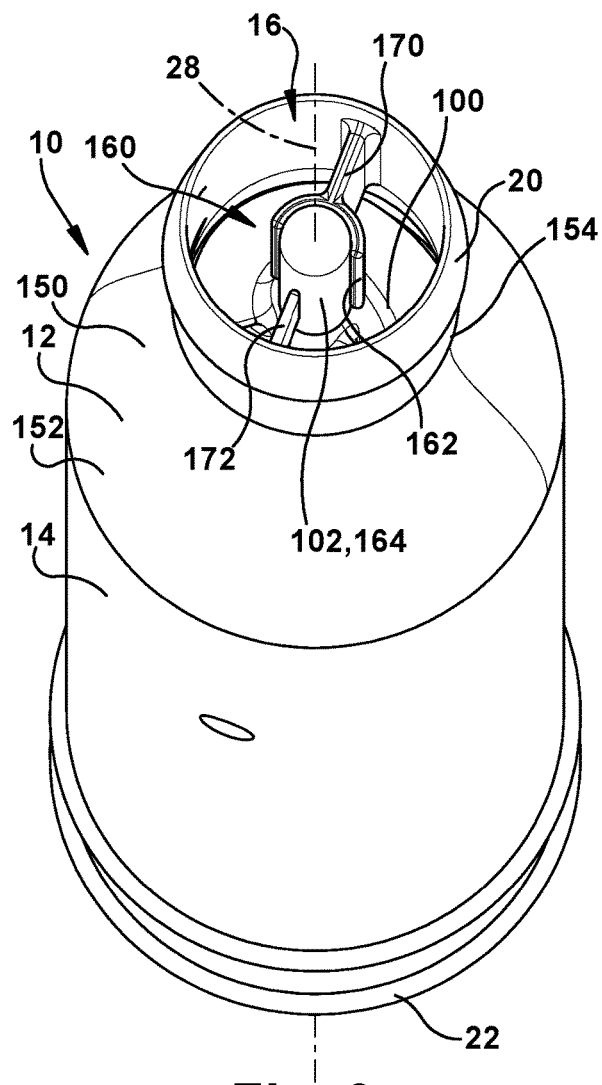
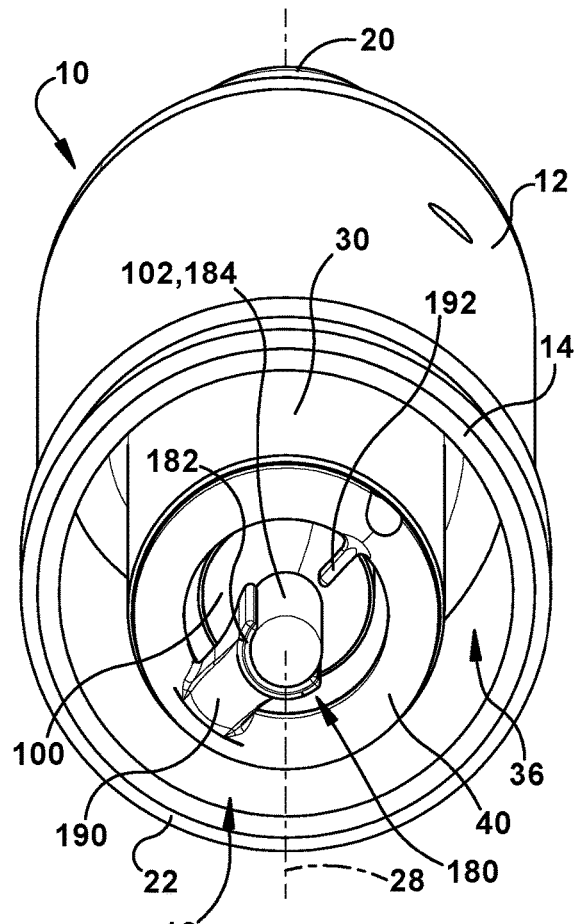
Fig. 6
Fig. 7

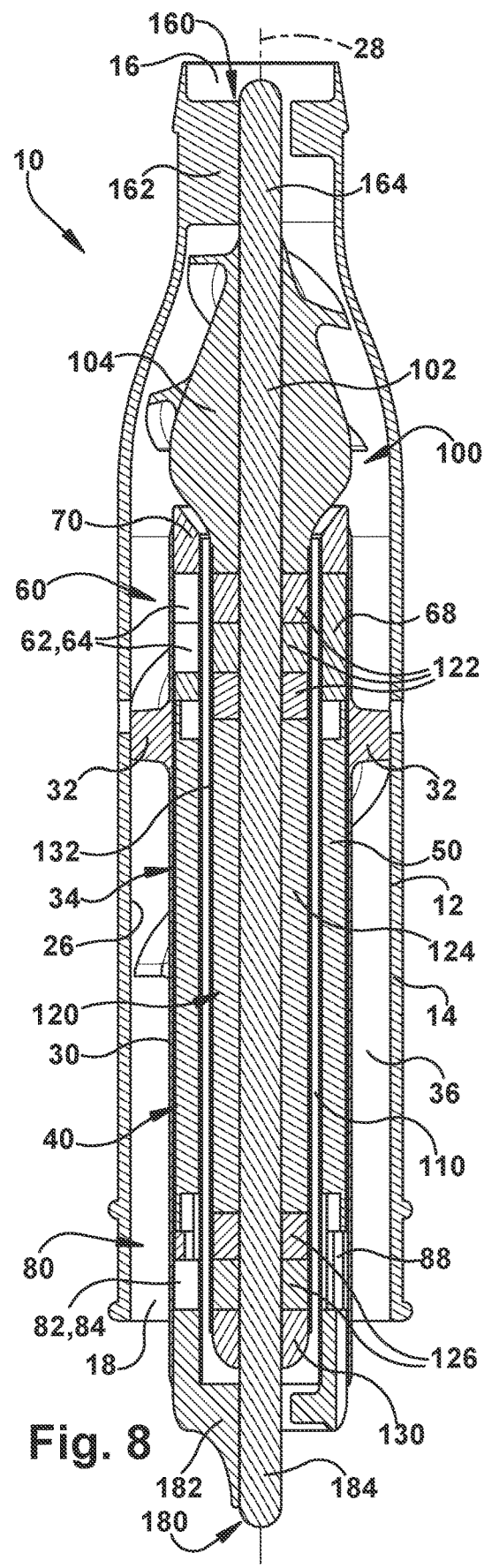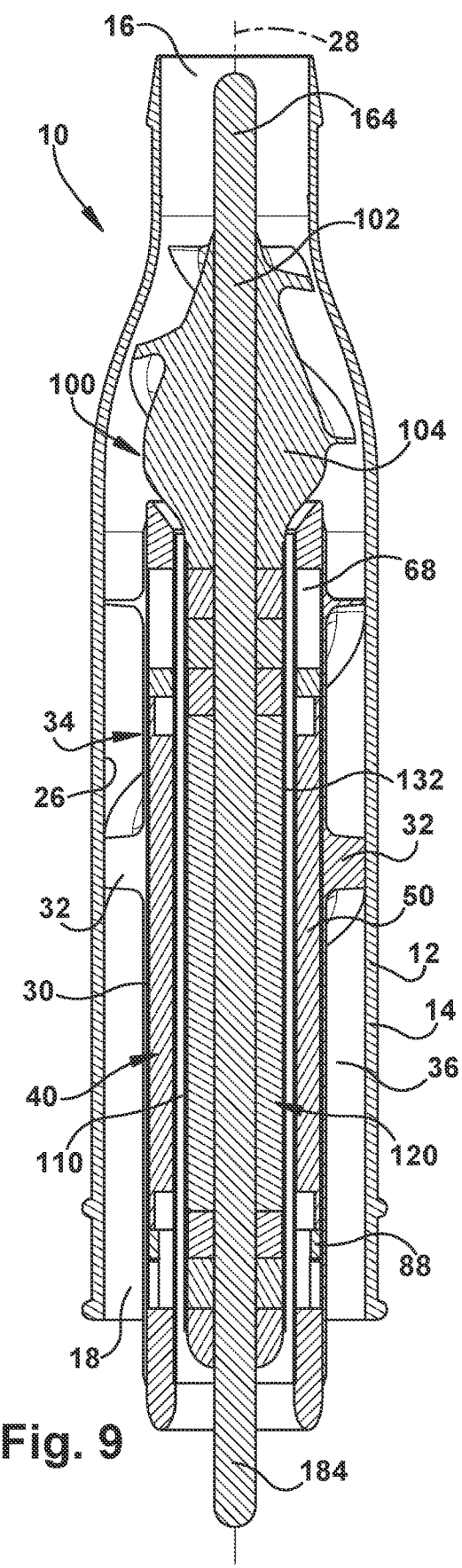

BLOOD PUMP WITH MAGNETICALLY LOADED PARTIAL ARC JOURNAL BEARING

RELATED APPLICATION

This application is a national phase application of and claims priority from PCT International Patent Application PCT/US2019/021964, filed Mar. 13, 2019, which claims the benefit of U.S. Provisional Application Ser. No. 62/642,756, filed 14 Mar. 2018 and entitled BLOOD PUMP WITH MAGNETICALLY LOADED PARTIAL ARC JOURNAL BEARINGS. The subject matter of each of the aforementioned applications is hereby incorporated by reference in its entirety.

GOVERNMENT FUNDING

This invention was made with government support under HL145819 and HL096144 awarded by the National Institutes of Health. The government has certain rights in the invention.

TECHNICAL FIELD

The invention relates to blood pumps, particularly implantable ventricular assist devices (VADs). More specifically, the invention relates to a VAD with an improved bearing structure.

BACKGROUND

Heart disease remains the single largest health problem in the U.S., and a large potential use for chronic blood pumps has been estimated. Coronary artery disease is the most common cause of death for both sexes, claiming nearly 500,000 lives annually while also contributing to hundreds of thousands of additional deaths. Heart failure is a common mode of death in many clinically relevant scenarios, e.g., as a complication of myocardial infarction, due to primary myocardial diseases or as a complication of cardiac surgical or catheter interventional procedures. Heart failure has been called a new epidemic. The ability to address more acute forms of death from heart disease and stroke results in greater numbers of patients who survive, only to experience long-term congestive heart failure.

The clinical need for implantable blood pumping has a wide range of applications, from permanent, total artificial hearts (TAHs) to short-term, partial circulatory support required for minimally invasive cardiac surgery or interventional cardiology procedures. As cardiac pharmacology and cell/gene therapy advance, bridge to recovery may become a major application for implantable blood pumps.

Ventricular assist devices (VADs) are implantable blood pumps that assist the pumping function native heart ventricle when the ventricle is unable to do so on its own. For example, an implanted VAD can take half the load off a failing ventricle, which can result in increased, stable output from less loaded ventricle. How to precisely define the role of VADs in cardiac medicine is subject to research and debate, due to the wide range of possibilities for their implementation. VADs can, for example be used as a destination therapy, bridge to transplant, bridge to recovery, bridge to definitive therapy and possibly other variants.

Regardless of the implementation, certain VAD features are emerging as important factors in determining the viability of their use, such as:

Adequate output to truly make a difference to the patient, realizing that an unloaded ventricle will frequently show significant restoration of function.
Reliability through the period of use, however long that might turn out in reality to be after support is instituted.
Ease of use.
Minimal morbidities associated with use, such as those resulting from major surgical invasion, bleeding, or thrombosis.
High costs resulting from hardware complexity or demanding post-operative care.

VAD technology is not without challenges. Large devices can result in extensive tissue/organ displacement and large pockets, which can further weaken already very ill patients. This can also provide locations for bacterial and fungal colonization, and can result in extensive adhesions impeding later surgeries. Internally, moving parts can create high shear stresses acting on the pumped blood, which can result in hemolysis, shortening red blood cell life and disturbing both platelet and leukocyte function. Another challenge is the formation of thrombosis and/or other systemic coagulation pathologies on pump surfaces, which can, over time, embolize. While anticoagulation protocols do exist, they can limit a clinician's ability to respond to other patient issues.

SUMMARY

A rotary dynamic blood pump includes a rotating assembly, or rotor, supported radially by a stator via small hydrodynamic bearings located at the front (i.e., upstream) and the rear (i.e., downstream) ends of the pump. The bearings are configured as journal bearings in which the rotor includes journal portions at its front and rear ends that are received in bushings on the stator. Uniquely, the bearings are located in a significant blood flow stream of the device, and the unloaded side of the bearing left open to the blood flow. This "open" bearing configuration refers to the fact that the bushings have an open or partial arc configuration. Unlike a typical journal bearing configuration in which the bushing encircles or extends around the entire the circumference of the journal, the partial arc bushing partially encircles, i.e., extends around only a portion of the circumference of the journal.

The blood immersed, hydraulic partial arc journal bearing configuration causes the bearings themselves, i.e., the journal and the bushing, to be continuously bathed in flowing blood. The bearings are fully hydrodynamic, with no contacting parts. The journals ride on a thick, low shear stress fluid, i.e., blood, films that continuously flow over the bushing. Unlike other hydrodynamic bearing blood pumps, the bearings themselves are disposed in a major blood flow path as opposed to a minor secondary path, or in a closed cavity. Because of this, blood exposure time to the bearing fluid stresses is minimized, which allows for reduced red cell destruction and platelet activation. The greater volume of blood flow improves heat removal.

The partial arc journal bearing configuration is facilitated, in part, by unidirectional, well-defined, magnetic loading, which holds the rotor journals in/on the arcs of their respective bushings. The pump has an elongated, axial structure in which the stator includes a housing in which the rotating assembly ("rotor") is supported. The rotor includes an impeller that draws blood axially into a front-located inlet and pumps the blood through the housing, discharging it through an outlet. The rotor also includes motor magnets that cooperate with stator mounted motor windings/back iron to produce rotation. The rotor journals are located at the front and rear ends of the rotor and ride in their corresponding stator-supported partial arc bushings.

The magnetic loading is facilitated by magnetic bearings that serve both as axial bearings for the rotor and also to radially load the partial arc journal bearing. The magnetic bearings are configured to exert a net radial pull on the rotating assembly that urges the rotor journals into their respective partial arc bushings. In operation, the journals ride hydrodynamically on a blood film that constantly flows over the bushing. This axial bearing configuration thus maintains the axial position of the rotor relative to the stator while, at the same time, maintaining the rotor journals in their partial arc bushings. Because the net radial pull is magnetic, the bearing system is not sensitive to the attitude or position of the pump.

In one example configuration, the magnetic bearings can include ring-shaped portions that exert a uniform pull that enforces the axial position of the rotor relative to the stator. Additionally, in this particular example configuration, the magnetic bearings also include partial ring-shaped or arced portions that exert a net radial pull on the rotor in the direction of the bushings. The radial pull on the rotor maintains the journals positioned or "seated" in their respective bushings.

Advantageously, unlike similarly sized conventional rotor supports, in addition to the partial arc journal bearings being continuously washed by blood flow, they also have their surfaces (i.e., the journal surface and the partial arc bushing surface) separated by a hydrodynamically generated, wear-free fluid film. This not only improves the performance of the pump in terms of preventing thrombosis and coagulation, it also reduces the complexity of the pump over that of conventional, new generations of magnetic bearing pumps. In addition to the good blood washing, the partial arc bearing can be designed to have a very thick, low blood shear film without becoming hydrodynamically unstable which is an issue with fully cylindrical bearings. The fluid stresses between rotating and stationary bearing surfaces and the construction tolerances can be more favorable than conical bearing structures. As such, the pump configuration can lend well to implementation as a circulatory support device, such as a VAD.

The hydraulic partial arc journal bearing configuration is readily adaptable to many surgical approaches. For example, in one configuration, the blood pump can be implemented as a VAD packaged to suit an intrathoracic implant via port surgery for medium term to permanent ventricular support. In addition to its anti-coagulation and/or thrombosis features, the hydraulic partial arc journal bearing configuration can also exhibit excellent hydraulic performance, low hemolysis, acceptable surface temperatures, and freedom from axial and radial wear.

The blood pump can provide several advantageous characteristics, such as minimum size, long term durability, low bleeding or thrombosis risk, relatively low cost and ease of implant/removal. The blood pump can be effective clinically and economically for resuscitation and bridge-to-transplant, definitive treatment, and recovery applications while having long term durability for cases that are intended or become permanent. The blood pump can provide a level of circulatory support well beyond inherently temporary pump design approaches, yet without the requirement of invasive implantation techniques. The durability and flow capacity goes beyond current equivalently sized blood pumps. The small size of the device also provides great flexibility in terms of patient age, size and implant approach. With simple housing design modifications, the pump can be configured for different clinical modes of application, including conventional extravascular (EVP), "pacemaker pocket" and intravascular (transvalvular or transapical) pump (IVP) implants. Left and right side support are possible, as are pediatric and single ventricle circulation support.

In operation, the pump can have a flow capacity of 3 l/min or higher at a pressure rise of 60 mm Hg. Flows will be higher or lower, depending on pump rotational speed and pressure differential. Blood flowing over the motor and through the motor gap carries away heat, before joining the main outflow path.

The design of the blood pump is smaller than any equally durable, equal flow output device, thereby fitting more patients more easily. The output is high enough to unload a failing ventricle, allowing stabilization and effective use of residual ventricular capacity. The small size makes the technology feasible for a wide range of patient sizes. The partial arc journal bearing design does not create the spaces, surfaces, crevices, etc. typically seen in conventional bearing designs, such as pin or ball supported rotors, and thus avoids the deposition and thromboembolism issues associated therewith.

The minimally invasive implantation techniques facilitated by this small design does not necessitate the coring-out of tissue from the ventricular apex. This reduced surgical invasiveness leads to quicker recovery, reduced risk of infection, and earlier discharge. The pump design is also conducive to the use of implanted controllers, diagnostic telemetry, and transcutaneous energy transmission systems (TETSs) as part of the system to eliminate the need for a percutaneous drive line.

According to one aspect, a blood pump includes a pump housing having a pump inlet and a pump outlet spaced apart along a longitudinally extending central pump axis. The blood pump also includes a rotating assembly comprising an impeller. The blood pump further includes partial arc journal bearings that support the rotating assembly for rotation in the housing. The rotating assembly is rotatable relative to the housing to pump blood from the pump inlet to the pump outlet.

According to another aspect, alone or in combination with any other aspect, the blood pump includes magnetic rings that exert a net radial force on the rotating assembly that maintains the rotating assembly seated in the partial arc journal bearings.

According to another aspect, alone or in combination with any other aspect, the magnetic rings maintain the axial position of the rotating assembly in the housing.

According to another aspect, alone or in combination with any other aspect, the magnetic rings include one or more magnets configured to produce a region of increased magnetic flux density pulls the rotating assembly into the partial arc journal bearings.

According to another aspect, alone or in combination with any other aspect, the blood pump also includes a stator assembly supported in the housing. The stator assembly includes motor stator windings, a front magnetic bearing stator, and a rear magnetic bearing stator. The rotating assembly also includes motor rotor magnets that align axially with the motor stator windings, a front magnetic bearing rotor that aligns with the front magnetic bearing stator, and a rear magnetic bearing rotor that aligns with the rear magnetic bearing stator.

According to another aspect, alone or in combination with any other aspect, the front and rear magnetic bearing stators each include one or more magnetic rings configured to produce a region of increased magnetic flux density on a bushing side of the pump. The front and rear magnetic bearing rotors include one or more magnetic rings in a full ring configuration. The front and rear magnetic bearing stators are configured to act on the front and rear magnetic bearing rotors to exert a net radial force on the rotating assembly that pulls the rotating assembly into the partial arc journal bearings.

According to another aspect, alone or in combination with any other aspect, the front and rear magnetic bearing stators are permanent magnet partial rings. The permanent magnet partial rings are positioned on the bushing side of the pump.

According to another aspect, alone or in combination with any other aspect, the rotating assembly includes a rotor shaft, an impeller mounted toward a front end portion of the rotor shaft, front magnetic bearing rotor magnet rings mounted on the rotor shaft adjacent the impeller, motor rotor magnets mounted on the rotor shaft adjacent the impeller front magnetic bearing rotor magnet rings, and rear magnetic bearing rotor magnet rings mounted on the rotor shaft adjacent the motor rotor magnets. A front end portion of the rotor shaft extends forward of the impeller and defines a front journal of the front partial arc journal bearing. A rear end portion of the rotor shaft extends rearward of the rear magnetic bearing rotor magnet rings defines a rear journal of the rear partial arc journal bearing.

According to another aspect, alone or in combination with any other aspect, the stator assembly includes a stator housing, a motor stator supported in the stator housing, front magnetic bearing stator magnetic rings mounted on the stator housing in front of the motor stator, and rear magnetic bearing stator magnetic rings mounted on the stator housing to the rear of the motor stator.

According to another aspect, alone or in combination with any other aspect, each of the partial arc journal bearings includes a cylindrical journal component of the rotating assembly and a bushing component fixed to the housing. The bushing has a partial arc configuration extending partially around the circumference of the journal.

According to another aspect, alone or in combination with any other aspect, the blood pump also includes magnetic rings that help constrain axial movement of the rotating assembly relative to the housing. The magnetic rings are configured to exert a net radial force on the rotating assembly that pulls the journals into their associated bushings.

According to another aspect, alone or in combination with any other aspect, the partial arc journal bearings is configured such that the partial arcs of the bushings are radially aligned with the magnetic rings.

According to another aspect, alone or in combination with any other aspect, the bushings extend radially 90-300 degrees around the circumference of their associated journals.

According to another aspect, alone or in combination with any other aspect, the bushings are aligned with each other radially about the pump axis.

According to another aspect, alone or in combination with any other aspect, the centers of the partial arcs of the bushings are positioned on the pump axis.

According to another aspect, alone or in combination with any other aspect, the front partial arc journal bearing is positioned in the pump inlet and the rear partial arc journal bearing is positioned in the pump outlet.

According to another aspect, alone or in combination with any other aspect, the pump housing comprises an inner housing and an outer housing between which an axially extending primary flow channel is defined. The blood pump is configured to pump blood through the primary flow channel.

According to another aspect, alone or in combination with any other aspect, the primary flow channel is annular and extends outside the stator assembly and the rotating assembly.

According to another aspect, alone or in combination with any other aspect, the helical flow straightening vanes extend between the inner and outer housings in the primary flow channel.

DRAWINGS

Figure 4:
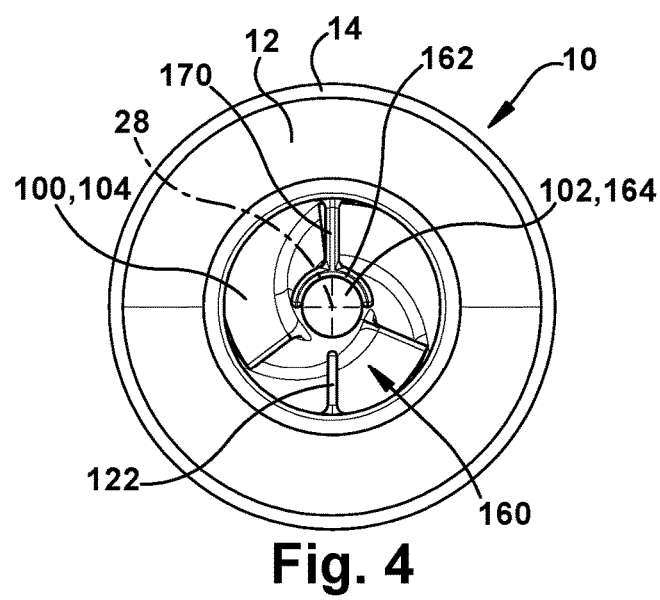
Figure 5:
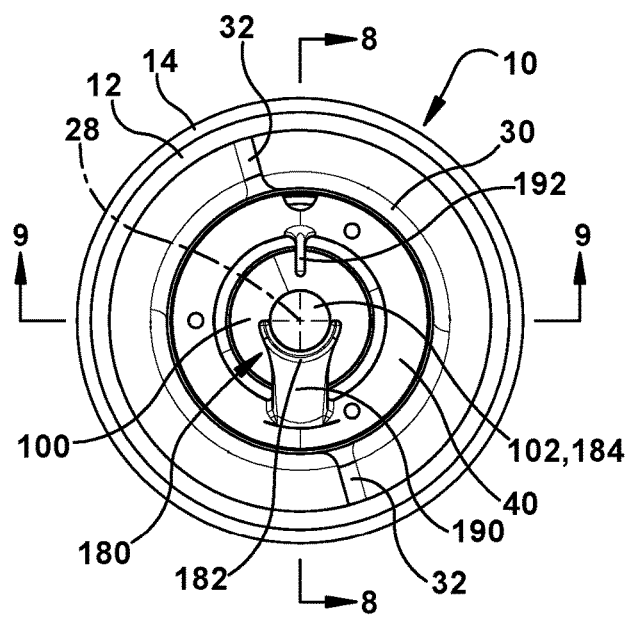
Figure 10:
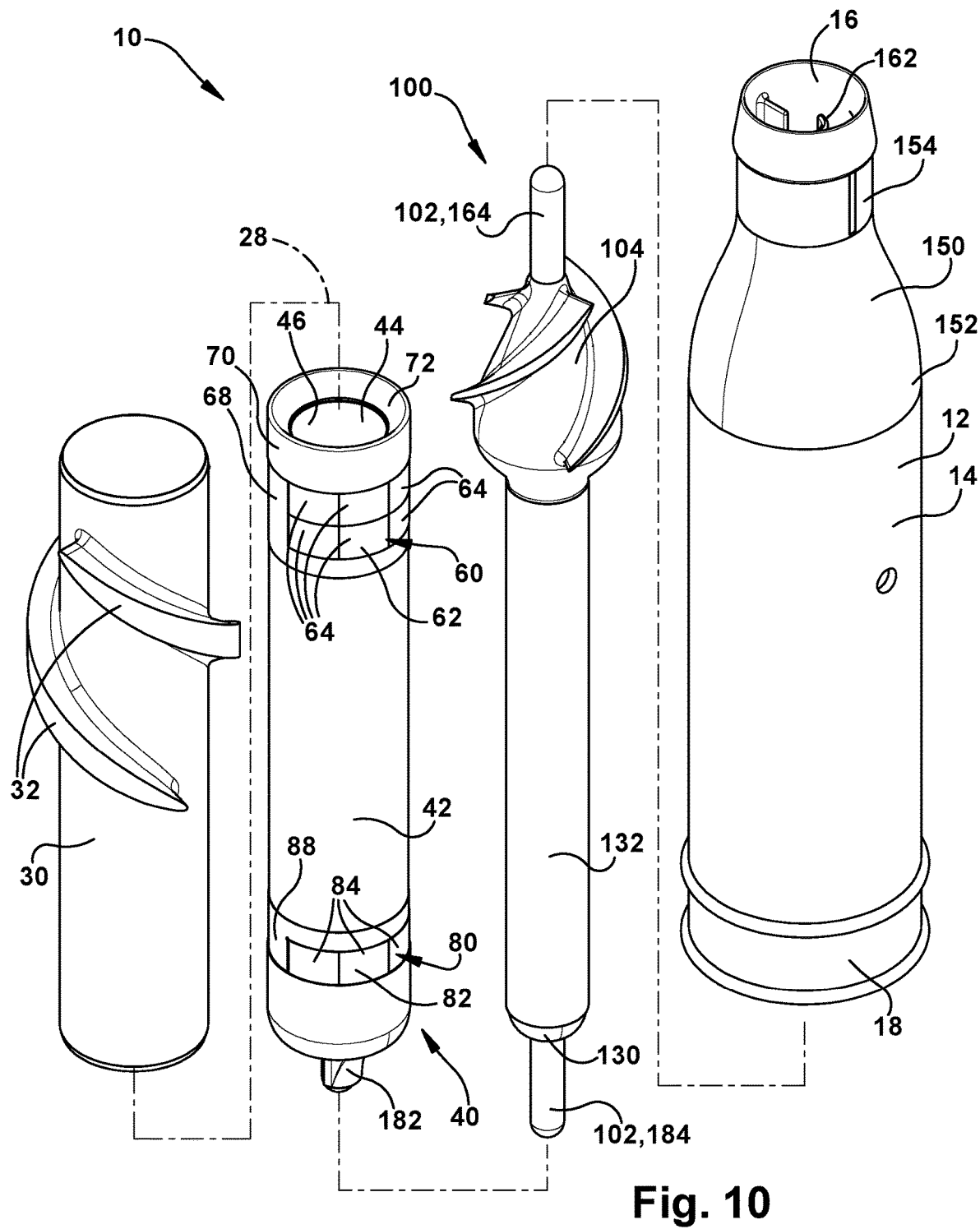
Figure 11:
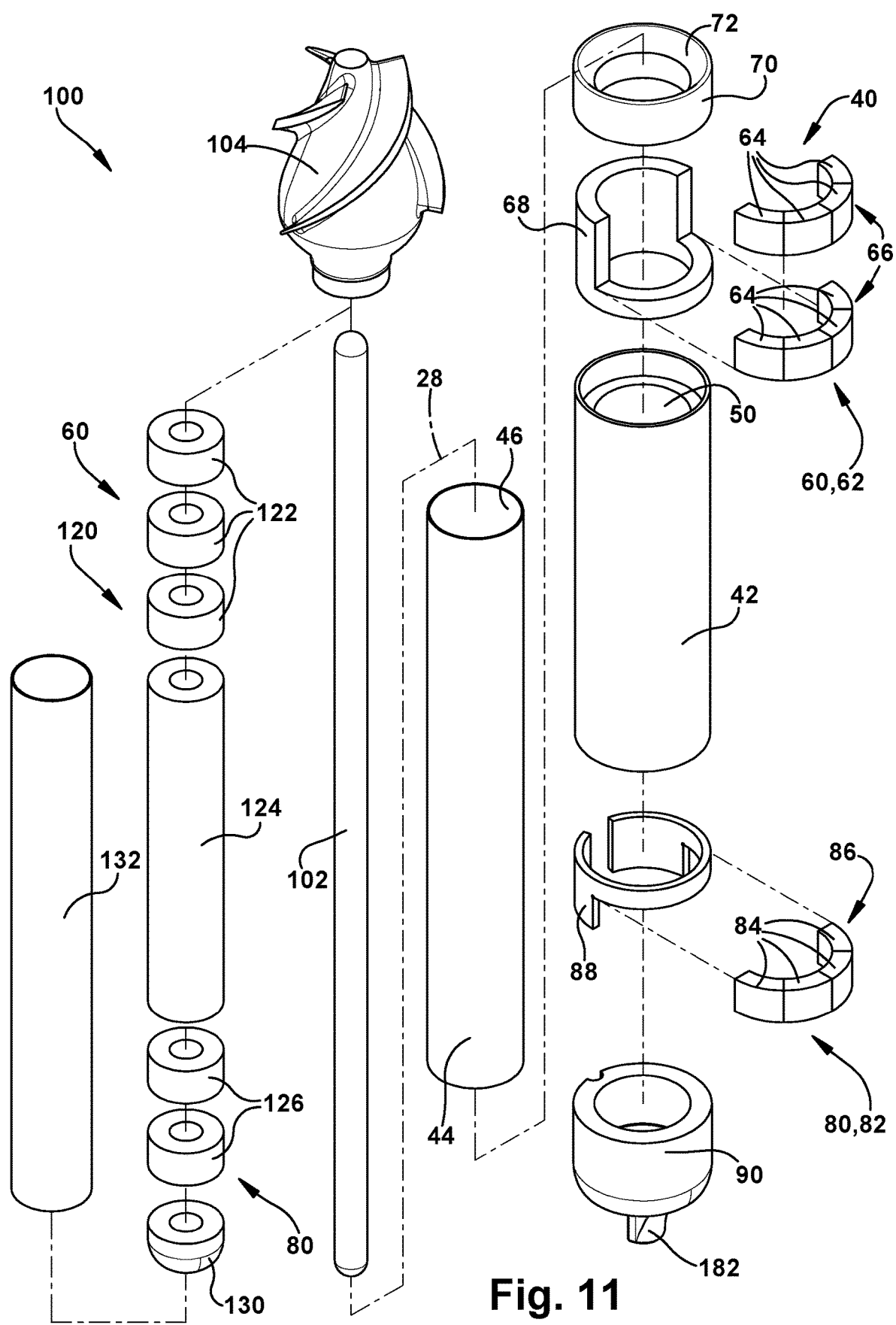
Figure 12:
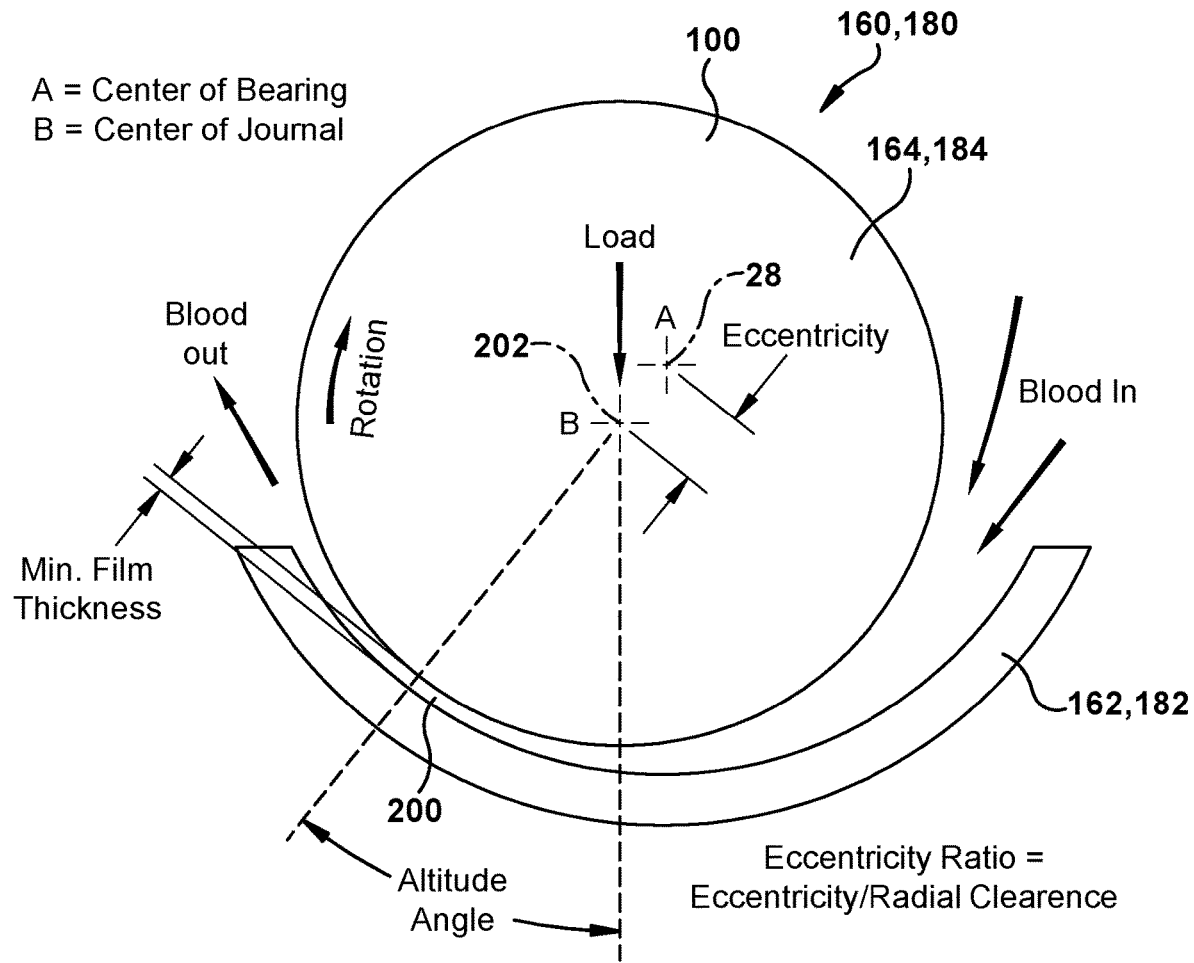

FIGS. 1 and 2 are perspective views of a blood pump.
FIG. 3 is a side view of the blood pump.
FIG. 4 is a front end view of the blood pump.
FIG. 5 is a rear end view of the blood pump.
FIG. 6 is a perspective top view of the blood pump.
FIG. 7 is a perspective bottom view of the blood pump.
FIG. 8 is a section view of the blood pump taken generally along line 8-8 in FIG. 5.
FIG. 9 is a section view of the blood pump taken generally along line 9-9 in FIG. 5.
FIG. 10 is an exploded view of the blood pump.
FIG. 11 is an exploded view of a portion of the blood pump.
FIG. 12 is a schematic view of a portion of the blood pump.

DESCRIPTION

A rotary dynamic blood pump 10 has a generally cylindrical configuration and is designed to move blood in a generally axial direction from a front or inlet end 20 of the pump to a rear or outlet end 22 of the pump. In this description, certain components may be described as having a front end and/or a rear end, or being located or positioned at or near a front end or a rear end of the blood pump 10 or components thereof. In these instances, the "front" or "front end" is meant to refer to the inlet end 20 of the blood pump 10 or components thereof, and the "rear" or "rear end" is meant to refer to the outlet end 22 of the blood pump or components thereof. Accordingly, reference can be made herein interchangeably to the front end or inlet end, as well as the rear end and/or outlet of the pump and its components.

While this invention is described with reference to a particular pump configuration illustrated in the figures, those skilled in the art will appreciate that the claimed features can cover a wide variety of alternative pump configurations. For example, the blood pump illustrated in the figures has a primarily axial flow pump configuration. The invention, however, is not limited to this flow configuration. Other configurations, such as radial flow or a combination of axial and radial flow (sometimes referred to as mixed flow), are entirely within the scope of the disclosed invention generally, and the unique bearing configuration specifically. Pumps having all of these flow configurations can utilize the bearing configuration disclosed herein and are therefore fall within the scope of the claims appended hereto.

Referring to FIGS. 1-9, the blood pump 10 includes a housing 12 comprising an outer pump housing 14 and an inner pump housing 30. The outer pump housing 14 has an elongated generally cylindrical configuration centered on a longitudinally extending pump axis 28. The outer pump housing 14 defines a pump inlet 16 at the front end portion 20 of the pump 10 and a pump outlet 18 at the rear end portion 22 of the pump. The front and/or rear end portions 20, 22 can include annular ribs that help facilitate connecting the pump with structures (not shown), such as inlet cannulas for directing blood flow into the pump inlet 16 and/or outlet cannulas for directing blood flow out of the pump outlet 18.

The inner pump housing 30 is supported by the outer pump housing 14 in an interior of the outer pump housing. The inner pump housing 30 has an elongated generally cylindrical configuration and extends coaxially with the outer pump housing 14 along the pump axis 28. The inner pump housing 30 includes a pair of vanes 32 that project from an outer surface 34 of the housing and extend helically about the axis 28. The helical vanes 32 extend axially along a portion of the length of the inner pump housing 30 from the front end portion 20 of the pump 10 to about the midpoint along the length of the inner pump housing. The configuration of the helical vanes 32, e.g., the number of vanes, the axial extent of the vanes, the helical pitch of the vanes, etc. can vary. In the assembled condition of the outer pump housing 14 and the inner pump housing 30, the helical vanes 32 extend from the outer surface 34 of the inner pump housing 30 to an inner surface 26 of the outer pump housing.

The blood pump 10 also includes a stator assembly 40 that is supported inside the inner pump housing 30. The stator assembly 40 includes a cylindrical elongated stator housing 42 and a motor stator 50 supported by the stator housing 42. The motor stator 50 is shown schematically and can be of any conventional design including, for example, stator windings and a stator back iron that supports the windings. In this example configuration of the motor stator 50, the stator windings and back iron can have any conventional motor stator configuration, such as a racetrack wound stator configuration.

The stator assembly 40 also includes front and rear magnetic bearing stators 62 and 82, respectively, supported by the stator housing 42. The front and rear magnetic bearing stators 62, 82 are components of front and rear magnetic bearings 60, 80, respectively, of the blood pump 10. The front and rear magnetic bearing stators 62, 82 are magnetic rings, each of which includes one or more permanent magnets 64 and 84, respectively. "Magnetic rings," as used herein, can include complete ring configurations (i.e., closed rings) or partial ring configurations (i.e., partial or open rings, i.e., arc-shaped).

In the illustrated example configuration, the magnets 64, 84 of the magnetic bearing stators 62, 82 are arranged radially in partial rings along the circumference of the stator housing 42 spaced equidistantly from the axis 28. The magnets 64, 84 do not extend about the entire circumference of the stator housing 42. Instead, the magnets 64, 84 extend in a partial ring configuration along a portion of the circumference only. In the illustrated example configuration, the radial extent of the magnets 64, 84 is about 180 degrees about the circumference of the stator housing 42. The radial extent of the magnets 64, 84 could vary, for example, from 90-300 degrees.

The front magnetic bearing stator 62 and rear magnetic bearing stator 82 each include at least one partial ring of magnets 64, 84. In the example configuration, the front magnetic bearing stator 62 includes two partial rings 66 and the rear magnetic bearing stator 82 includes a single partial ring 86. The number of partial rings 66, 86 included in each magnetic bearing stator 62, 82 could differ. Also, in the example configuration, each of the partial rings 66, 86 includes three permanent magnets 64, 84. Each partial ring could, however, include any number of permanent magnets 64, 84, i.e., one or more. Further, in addition to the partial rings 66, 86, each magnetic bearing stator 62, 82 could additionally include one or more full magnetic rings.

In the example configuration, the stator assembly 40 includes a front magnet support 68 for supporting the magnets 64 and a rear magnet support 88 for supporting the magnets 84. The front magnet support 68 is configured to be seated or otherwise connected to a front end of the stator housing 42. The rear magnet support 88 is configured to be seated or otherwise connected to a rear end of the stator housing 42. The stator assembly 40 can also include an inner sleeve 44 positioned coaxially with the stator housing 42 and extending along its length to define an inner surface 46 of the stator assembly. The inner sleeve 44 can be constructed of a material that is biologically compatible with blood so as to serve as a barrier between the pumped blood and the internal stator components (i.e., the motor stator 50 and magnets 64, 84).

A front end cap 70 connects with the stator housing 42 and/or the front magnet support 68 and forms the terminal front end of the stator assembly 40. The front end cap 70 includes an annular end surface 72 that is recessed and has a generally curved configuration. A rear end cap 90 connects with the stator housing 42 and/or the rear magnet support 88 and forms the terminal rear end of the stator assembly 40.

The blood pump 10 also includes a rotating assembly or rotor 100 that is supported for rotation in the pump housing 12 generally about the pump axis 28. By "generally" about the pump axis 28, it is meant to recognize that the rotating assembly is supported on a hydrodynamic bearing structure (described in detail below) that allows for some radial shifting of the rotating assembly relative to the stator assembly 40. As The rotating assembly 100 includes an internal rotor shaft 102 and an impeller 104 connected to a front end of the rotor shaft. Components of the rotating assembly 100 extending rearward from the impeller 104 define a rotor body 106. A cylindrical front journal 164 extends coaxially with the rotor shaft 102 and impeller 104 from a front end of the impeller. A cylindrical rear journal 184 extends coaxially with the rotor shaft 102 and impeller 104 from a rear end of the main shaft.

The rotating assembly 100 includes components housed within the rotor body 106 that together define a motor rotor 120 that cooperates with the motor stator 50 to produce rotational motion of the rotating assembly during operation of the blood pump 10. The rotor shaft 102 extends the entire length of the rotating assembly, with a front end portion defining the front journal 164 and a rear end portion defining the rear journal 184. The impeller 104 is fixed to the rotor shaft 102 toward the front end portion of the internal shaft. One or more front magnetic bearing rotor magnets 122 are mounted to the rotor shaft 102 adjacent the impeller 104, followed by one or more motor rotor magnets 124 and then one or more rear magnetic bearing rotor magnets 126. The front and rear magnetic bearing rotor magnets 122, 126 are components of the front and rear magnetic bearings 60, 80, respectively.

A rotor end cap 130 is fixed to the rotor shaft 102 adjacent to, and rearward of, the rear magnetic bearing rotor magnets 126. The portion of the internal shaft 120 defining the rear journal 184 extends rearward from the rotor end cap. The rotating assembly 100 can also include an outer sleeve 132 positioned coaxially with the rotor shaft 102 and extending over the outer circumferential surfaces of the front magnetic bearing rotor magnets 122, the motor rotor magnets 124, and the rear magnetic bearing rotor magnets 126. The outer sleeve 132 defines the outer surface of the rotor body 106 of the rotating assembly 100 extending between the impeller 104 and the end cap 130. The outer sleeve 132 can be constructed of a material that is biologically compatible with blood so as to serve as a barrier between the pumped blood and the internal rotor components (i.e., the motor rotor magnets 124 and magnetic bearing magnets 122, 126). The rotor shaft 102, and thus the front and rear journals 164, 184, as well as the impeller 104, can also be constructed of a material that is biologically compatible with blood.

In the assembled condition of the blood pump 10, the rotating assembly 100 is supported in the housing 12 with the rotor body 106 positioned in a cylindrical space defined by the inner housing 30. This positions the magnetic bearing rotor magnets 122, 126 in axial alignment with the magnetic bearing stator magnets 64, 84, respectively. This also positions the motor magnets 124 in axial alignment with the motor stator 50.

The rotating assembly 100 is supported in the pump housing 12 by front and rear bushings 162 and 182, respectively. The front bushing 162 is positioned at the front end portion 20 of the pump housing 12 in the pump inlet 16. The rear bushing 182 is positioned at the rear end portion 22 of the housing 12 at the pump outlet 18. In the example configuration, the front bushing 162 is connected to or formed as an integral portion of the outer pump housing 14. More specifically, in the example configuration, the front end portion of the outer pump housing 14 has tapered configuration with a tapered sidewall 150 that reduces the diameter of the outer pump housing from a large diameter portion 152 to a smaller diameter portion 154 that defines the front end portion 20 and the pump inlet 14. The front bushing 162 could be configured in an alternative manner, such as a separate component that is fixed to the pump housing 12.

The rear bushing 182 is connected to or formed as an integral portion of a rear end portion of the stator assembly 40. In the example configuration, the rear bushing 182 is formed as an integral portion of the rear end cap 90 of the stator assembly 40, and is thereby connected to the stator housing 42 and/or the rear magnet support 86 and forms the terminal rear end of the stator assembly 40. When the blood pump 10 is assembled, the rotating assembly 100 is supported by the bushings 162, 182 inside the pump housing 12 for rotation about the axis 28.

In the assembled condition of the blood pump 10, the space between the inner pump housing 30 and the outer pump housing 14, i.e., the between the outer surface 34 and the inner surface 26, defines an annular primary flow channel 36 that extends along the length of the pump 10 from the pump inlet 16 to the pump outlet 18. The helical vanes 32 are positioned in the primary flow channel 36. A radial motor gap 110 is defined between the outer sleeve 132 of the rotating assembly 100 and the inner sleeve 44 of the stator assembly 40. The motor gap 110 is thus defined between the outer surface of the rotor shaft 104 and the inner surface 46 of the stator assembly 40 and extends the length of the rotating assembly 100 from the impeller 104 to the rotor end cap 130.

The front and rear bushings 162 and 182 in combination with the front and rear journals 164 and 184 define respective front and rear journal bearings 160 and 180, respectively. More specifically, the front and rear journal bearings 160 and 180 are partial arc journal bearings. As best shown in FIGS. 6-9, the front and rear bushings 162, 182, which support the front and rear journals 164, 184 have a partial arc configuration. In the example configuration, the bushings 162, 182 extend about 180 degrees about their respective journals 164, 184. The radial extent of the front and rear bushings 162, 182 could, however, vary. For instance, the front and rear bushings 162, 182 could extend in the aforementioned range of 90-300 degrees about the journals 164, 184.

The front bushing 162 is positioned at the front end 20 of the pump 10 in the pump inlet 16. The front bushing 162 is supported by a base portion 170 that extends radially inward from the sidewall of the outer pump housing 14. The length of the base portion 170 can be selected such that the center of the arc of the front bushing 162 is positioned on the pump axis 28. A stop piece 172 extends radially inward from the sidewall of the outer pump housing 14 from a position radially opposite the base portion 170. The length of the stop piece 172 is configured such that it terminates a distance from the pump axis 28 that is greater than the radius of the front journal 164. Because of this, the tip of the stop piece 172 is spaced from the front journal 164. The stop piece 172 acts as an inlet flow guide vane and further prevents the journal 164 from becoming unseated from the bushing 162 in response to extraordinary shock or other unexpected forces.

The rear bushing 182 is positioned at the rear end 22 of the pump 10 at the pump outlet 18. The front and rear bushings 162, 182 are aligned radially with each other with respect to the axis 28. The rear bushing 182 is supported by a base portion 190 that extends radially inward from a sidewall of the rear end cap 90 of the stator assembly 40. The length of the base portion 190 can be selected such that the center of the arc of the rear bushing 182 is positioned on the pump axis 28. A stop piece 192 extends radially inward from the sidewall of the rear end cap 90 from a position radially opposite the base portion 190. The length of the stop piece 192 is configured such that it terminates a distance from the pump axis 28 that is greater than the radius of the rear journal 184. Because of this, the tip of the stop piece 192 is spaced from the rear journal 184. The stop piece 192 acts as an outlet flow guide vane and further prevents the journal 184 from becoming unseated from the bushing 182 in response to extraordinary shock or other unexpected forces.

When the blood pump 10 is assembled, the front and rear journal bearings 160, 180 support the rotating assembly 100 for rotation about the axis 28. The front and rear magnetic bearings 60, 80 help maintain the axial position of the rotating assembly 100 relative to the stator assembly 40. The front and rear magnetic bearings 60, 80 oppose axial movement of the rotating assembly 100 created in response to axial forces acting on the rotor caused by hydrodynamic pumping forces created by the interaction of the impeller 104 with the pumped blood. The magnetic attraction between the magnetic bearing stator magnets 64, 84 and the magnetic bearing rotor magnets 122, 126 helps maintain the position of the rotating assembly 100 throughout the range of pump flow rates.

In one example configuration of the magnetic bearings 60, 80, the magnets can be selected such that axial pull of the rotating assembly 100 cannot overcome their axial magnetic strength. In another example configuration of the front and rear magnetic bearings 60, 80, the magnets can be selected to produce a net axial pull on the rotating assembly 100 relative to the stator 40 in a direction opposite the axial forces acting on the rotor due to the hydrodynamic pumping forces of the impeller 104. In this manner, these axial hydrodynamic pumping forces can be canceled or partially cancelled by the net magnetic axial pull of the magnetic bearings 60, 80.

Additionally, when the blood pump 10 is assembled, the front and rear magnetic bearings 60, 80 also help enforce a radial pull on the rotating assembly 100 relative to the stator 40 so that the front and rear journals 164, 184 are maintained positioned in the front and rear bushings 162, 182, respectively. This maintains the rotating assembly 100 seated in the journal bearings 160, 180. This is due, at least in part, to the configuration of the front and rear magnetic bearing stators 62, 82. More specifically, in the illustrated example configuration, this is due to the partial magnet rings 66, 86, that form or partially form the front and rear magnetic bearing stators 62, 82. The magnet partial rings 66, 86 are positioned at a radial position on the stator assembly 40 that coincides with the radial positions of the front and rear bushings 162, 182. The magnet partial rings 66, 86 act on the magnetic bearing rotor magnets 122, 126 to pull those magnets, and thus the rotating assembly 100, radially to seat the journals 164, 184 in the bushings 162, 182.

The magnet partial rings 66, 86 create a magnetic field that has a region of increased magnetic flux density on the bushing side of the pump 10. "Bushing side" is meant to refer to the radial position of the bushings 162, 182 on the pump 10 relative to the pump axis 28. Thus, the region of increased flux density is positioned or concentrated at a radial position relative to the pump axis 28 as the bushings 162, 182.

The region of increased magnetic flux density is created through the magnetic ring configuration of the front and rear magnetic bearing stators 62, 82. In the example configuration illustrated in the figures, the region of increased magnetic flux density is created by the partial ring configuration of the front and rear magnetic bearings 60, 80, which creates an asymmetric field concentrated on the bushing side of the pump 10. The front and rear bearings 60, 80 could, however, achieve the region of increased magnetic flux density on the bushing side of the pump 10 in a variety of manners.

For example, the region of increased magnetic flux density could be created by magnetic bearing stators 62, 82 having a magnetic ring configuration in which a full ring permanent magnet structure is thicker or has greater mass for producing the increased flux density region and is thinner or has less mass in other regions. As another example, the region of increased magnetic flux density could be created by magnetic bearing stators 62, 82 having a magnetic ring configuration in which a full ring bearing structure includes higher strength magnets in the high flux density regions and lower strength magnets in lower flux density regions.

As another example, the region of increased magnetic flux density could be created by magnetic bearing stators 62, 82 having a magnetic ring configuration in which a uniform, circular, full ring bearing structure could be shifted relative to the pump axis 28. In this configuration, the full magnetic rings of the stators 62, 82 would be positioned closer to the axis on the bushing side of the pump 10. This would create a region of increased magnetic flux density by shifting a uniform flux density of the full magnetic ring closer to the rotating assembly 100 on the bushing side of the pump 10.

As a further example, the region of increased magnetic flux density could be created by magnetic bearing stators 62, 82 having a magnetic ring configuration in which a full ring bearing structure has a non-circular and/or non-uniform shape. In this configuration, non-circular/uniform full magnetic rings can be configured to shift the region of increased magnetic flux density closer to the pump axis 28 and rotating assembly 100 on the bushing side of the pump 10.

As a further example, the region of increased magnetic flux density could be created by magnetic bearing stators 62, 82 having combinations of the features described above. For example, the magnetic bearing stators 62, 82 could have a magnetic ring configuration in which the magnets are arranged in an open ring/arc, have non-uniform shapes and/or regions of non-uniform mass, and have certain portions positioned closer to the pump axis 28 than others. As another example, the magnetic bearing stators 62, 82 could have a magnetic ring configuration in which the magnets are arranged in a closed ring, have non-uniform shapes and/or regions of non-uniform mass, and have certain portions positioned closer to the pump axis 28 than others. Those skilled in the art will appreciate that the magnetic bearing stators 62, 82 can have many other combinations of these features configured to produce the desired region of increased magnetic flux density.

Advantageously, the radial pull that seats the rotating assembly 100 in the journal bearings 160, 180 does not negatively affect the magnetic axial bearing functionality of the magnetic bearings 60, 80. The magnetic bearing rotor magnets 122, 126 extend the entire radius of the rotating assembly 100, so the magnetic axial pull that the magnetic bearings 60, 80 exert on the rotor is constant. Because the partial magnet rings 66, 86 are just that—partial—their magnetic strengths may be increased over that of a full ring magnetic bearing configuration for compensation but, functionally, their operation is not affected and the axial position of the rotating assembly 100 relative to the stator assembly 40 can be maintained. To produce the desired radial and axial loading of the rotating assembly 100, the magnetic bearings can adopt a Halbach array geometry to increase the magnetic field strength on the opposing sides of the stator and rotor magnets.

In operation, the blood pump 10 moves blood from the inlet 16 to the outlet 18 through the primary flow channel 36. The helical vanes 32 straighten the swirl induced by the impeller 104 so that the primary flow can be substantially straight or axial along the primary flow channel 36. A motor wash flows through the motor gap 110 which helps dissipate heat and helps prevent blood from collecting or being held static in the pump. Depending on the configuration of the pump 10 and the resulting fluid pressures in the pump, the wash flow can be in the same direction as the primary flow, i.e., front to back, or reversed, i.e., from back to front.

The partial arc journal bearings 160, 180 exhibit characteristics that are advantageous to the blood pumping performance of the pump 10. The partial arc journal bearings 160, 180 act as small hydrodynamic bearings located at the front (i.e., upstream) and the rear (i.e., downstream) ends of the rotating assembly 100. The bearings 160, 180 are located in the blood flow stream of the pump 10. The front journal bearing 160 is positioned in the pump inlet 16, so the blood entering the pump constantly circulates over/through the bearing. The rear journal bearing 180 is positioned at the pump outlet 18 where blood exiting the pump 10 flows over its structure.

FIG. 12 illustrates schematically the partial arc journal bearings 160, 180 during pump operation. As the rotating assembly 100 rotates (clockwise as illustrated in FIG. 12), the rotating journal 164, 184 draws blood into the thin gap between the journals and the bushings 162, 182 at one end radial end of the bushings (the right end in FIG. 12) and sends it out at the opposite end (the left end in FIG. 12). It is this layer of blood that forms what is referred to herein as the fluid-film barrier 200 between those components. The fluid-film barrier 200 avoids surface-to-surface contact between the bushings 162, 182 and the journals 164, 184, which reduces friction and wear and also damps undesirable mechanical vibrations. The thickness of the fluid-film barrier 200 is ideally in the range of thousandths to hundredths of a millimeter.

As shown in FIG. 12, during pump operation, loads applied to the impeller 104 and rotating assembly 100 cause the journals 164, 182 to shift laterally in the bushings 162, 182. This causes the rotating assembly 100 to shift such that the rotor axis 202, which is the axis of rotation, to shift away from the central pump axis 28. Thus, the fluid film barrier 200 does not have a uniform thickness. The region where the fluid film barrier 200 is thinnest is shifted (to the left in FIG. 12). The effective size or area of the thinnest region of the fluid film barrier 200 is small. This small fluid film barrier 200 produces lower viscous drag versus a full or circular bushing journal bearing configuration, which results in lower frictional power losses. The partial arc configuration further prevents the development of unstable hydrodynamic fluid forces that can cause a comparatively thick, low shear stress film circular bearing to go into a destructive whirl mode.

The implementation of the partial arc journal bearings 160, 180 provides stable hydrodynamic blood pump bearing support for the rotating assembly 100 that is located in the main blood flow path. The partial arc configuration can leave the journals open over 180 degrees, or more. This bearing design can provide wear-free support of the rotating assembly 100 while minimizing the time a blood cell spends in the minimum film thickness zone, with blood exchange being continual. Because of this, blood residence time in this high shear zone is extremely short. As a result, the partial arc journal bearing configuration of the blood pump 10 can exhibit high shear tolerance for both red cells, white blood cells, and platelets.

The partial arc journal bearings 160, 180 also help suppress cavitation. As described above, during pump operation, due to the loads applied to the bearings 160, 180 and the rotating assembly 100, the thickness of the fluid film barrier 200 is not constant. The flow pressure within the bearings 160, 180 across the fluid film barrier 200 also is not constant. When this flow pressure drops below the ambient pressure, air and other gases dissolved within the lubricant are released. This phenomenon, characteristic of loaded bearings, is known as cavitation or gaseous cavitation.

Parametric studies of different fluid film barrier thicknesses for the partial arc journal bearings 160, 180 have shown that the bearings 160, 180 function well over a range of tolerances on clearance, viscosity, speed and load. The blood pump 10 therefore can run at speeds slower than design speed without trouble. Similar studies show the attitude angle (see FIG. 12) maintains the journals 164, 184 stays well within the bushings 162, 182 and the eccentricity ratio (eccentricity/radial clearance; see FIG. 12) is large enough to ensure hydrodynamic stability with the partial arc geometry.

The foregoing has described a blood pump that implements partial arc journal bearings to provide improved resistance to thrombosis formation. While specific example configurations have been described, it will be apparent to those skilled in the art that various modifications thereto can be made without departing from the spirit and scope of the invention. Accordingly, the foregoing description of the example configuration are provided for the purpose of illustration only and not for the purpose of limitation.

I claim:
1. A blood pump comprising:
   a pump housing having a pump inlet and a pump outlet spaced apart along a longitudinally extending central pump axis;
   a rotating assembly comprising an impeller; and
   partial arc journal bearings that support the rotating assembly for rotation in the housing, wherein the rotating assembly is rotatable relative to the housing to pump blood from the pump inlet to the pump outlet, wherein each of the partial arc journal bearings comprises a cylindrical journal component of the rotating assembly and a bushing component fixed to the housing, the bushing having a partial arc configuration extending partially around the circumference of the journal;
   wherein the blood pump further comprises magnetic rings that help constrain axial movement of the rotating assembly relative to the housing, the magnetic rings being configured to exert a net radial force on the rotating assembly that pulls the journals into their associated bushings.

2. The blood pump recited in claim 1, wherein:
   the pump further comprises a stator assembly supported in the housing, the stator assembly comprising motor stator windings, a front magnetic bearing stator, and a rear magnetic bearing stator; and
   the rotating assembly comprises motor rotor magnets that align axially with the motor stator windings, a front magnetic bearing rotor that aligns with the front magnetic bearing stator, and a rear magnetic bearing rotor that aligns with the rear magnetic bearing stator.

3. The blood pump recited in claim 2, wherein the front and rear magnetic bearing stators each comprise one or more magnetic rings configured to produce a region of increased magnetic flux density on a bushing side of the pump, and wherein the front and rear magnetic bearing rotors comprise one or more magnetic rings in a full ring configuration, wherein the front and rear magnetic bearing stators are configured to act on the front and rear magnetic bearing rotors to exert a net radial force on the rotating assembly that pulls the rotating assembly into the partial arc journal bearings.

4. The blood pump recited in claim 3, wherein the front and rear magnetic bearing stators comprise permanent magnet partial rings.

5. The blood pump recited in claim 4, wherein the permanent magnet partial rings are positioned on the bushing side of the pump.

6. The blood pump recited in claim 2, wherein the stator assembly comprises:
   a stator housing;
   a motor stator supported in the stator housing;
   front magnetic bearing stator magnetic rings mounted on the stator housing in front of the motor stator; and
   rear magnetic bearing stator magnetic rings mounted on the stator housing to the rear of the motor stator.

7. The blood pump recited in claim 1, wherein the pump housing comprises an inner housing and an outer housing between which an axially extending primary flow channel is defined, the blood pump being configured to pump blood through the primary flow channel.

8. The blood pump recited in claim 7, wherein the primary flow channel is annular and extends outside the stator assembly and the rotating assembly.

9. The blood pump recited in claim 7, further comprising helical flow straightening vanes that extend between the inner and outer housings in the primary flow channel.

10. The blood pump recited in claim 1, wherein the magnetic rings maintain the axial position of the rotating assembly in the housing.

11. The blood pump recited in claim 1, wherein the magnetic rings comprise one or more magnets configured to produce a region of increased magnetic flux density that pulls the rotating assembly into the partial arc journal bearings.

12. The blood pump recited in claim 1, wherein the rotating assembly comprises:
a rotor shaft;
an impeller mounted toward a front end portion of the rotor shaft;
front magnetic bearing rotor magnet rings mounted on the rotor shaft adjacent the impeller;
the motor rotor magnets being mounted on the rotor shaft adjacent the impeller front magnetic bearing rotor magnet rings; and
rear magnetic bearing rotor magnet rings mounted on the rotor shaft adjacent the motor rotor magnets;
wherein a front end portion of the rotor shaft extending forward of the impeller defines a front journal of the front partial arc journal bearing, and wherein a rear end portion of the rotor shaft extending rearward of the rear magnetic bearing rotor magnet rings defines a rear journal of the rear partial arc journal bearing.

13. The blood pump recited in claim 1, wherein the bushings extend radially 90-300 degrees around the circumference of their associated journals.

14. The blood pump recited in claim 1, wherein the bushings are aligned with each other radially about the pump axis.

15. The blood pump recited in claim 1, wherein the centers of the partial arcs of the bushings are positioned on the pump axis.

16. The blood pump recited in claim 1, wherein the front partial arc journal bearing is positioned in the pump inlet and the rear partial arc journal bearing is positioned in the pump outlet.

17. The blood pump recited in claim 1, wherein the partial arc journal bearings are configured such that the partial arcs of the bushings are radially aligned with the magnetic rings.

18. A blood pump comprising:
a pump housing having a pump inlet and a pump outlet spaced apart along a longitudinally extending central pump axis;
a rotating assembly comprising an impeller; and
partial arc journal bearings that support the rotating assembly for rotation in the housing, wherein the rotating assembly is rotatable relative to the housing to pump blood from the pump inlet to the pump outlet, wherein each of the partial arc journal bearings comprises a cylindrical journal component of the rotating assembly and a bushing component fixed to the housing, the bushing having a partial arc configuration extending radially 90-300 degrees around the circumference of their associated journals.

19. The blood pump recited in claim 18, wherein:
the pump further comprises a stator assembly supported in the housing, the stator assembly comprising motor stator windings, a front magnetic bearing stator, and a rear magnetic bearing stator; and
the rotating assembly comprises motor rotor magnets that align axially with the motor stator windings, a front magnetic bearing rotor that aligns with the front magnetic bearing stator, and a rear magnetic bearing rotor that aligns with the rear magnetic bearing stator.

20. The blood pump recited in claim 19, wherein the front and rear magnetic bearing stators each comprise one or more magnetic rings configured to produce a region of increased magnetic flux density on a bushing side of the pump, and wherein the front and rear magnetic bearing rotors comprise one or more magnetic rings in a full ring configuration, wherein the front and rear magnetic bearing stators are configured to act on the front and rear magnetic bearing rotors to exert a net radial force on the rotating assembly that pulls the rotating assembly into the partial arc journal bearings.

21. The blood pump recited in claim 20, wherein the front and rear magnetic bearing stators comprise permanent magnet partial rings.

22. The blood pump recited in claim 21, wherein the permanent magnet partial rings are positioned on the bushing side of the pump.

23. The blood pump recited in claim 19, wherein the stator assembly comprises:
a stator housing;
a motor stator supported in the stator housing;
front magnetic bearing stator magnetic rings mounted on the stator housing in front of the motor stator; and
rear magnetic bearing stator magnetic rings mounted on the stator housing to the rear of the motor stator.

24. The blood pump recited in claim 23, further comprising magnetic rings that help constrain axial movement of the rotating assembly relative to the housing, the magnetic rings being configured to exert a net radial force on the rotating assembly that pulls the journals into their associated bushings.

25. The blood pump recited in claim 24, wherein the partial arc journal bearings are configured such that the partial arcs of the bushings are radially aligned with the magnetic rings.

26. The blood pump recited in claim 18, wherein the pump housing comprises an inner housing and an outer housing between which an axially extending primary flow channel is defined, the blood pump being configured to pump blood through the primary flow channel.

27. The blood pump recited in claim 26, wherein the primary flow channel is annular and extends outside the stator assembly and the rotating assembly.

28. The blood pump recited in claim 26, further comprising helical flow straightening vanes that extend between the inner and outer housings in the primary flow channel.

29. The blood pump recited in claim 18, wherein the magnetic rings maintain the axial position of the rotating assembly in the housing.

30. The blood pump recited in claim 18, wherein the magnetic rings comprise one or more magnets configured to produce a region of increased magnetic flux density that pulls the rotating assembly into the partial arc journal bearings.

31. The blood pump recited in claim 18, wherein the rotating assembly comprises:
a rotor shaft;
an impeller mounted toward a front end portion of the rotor shaft;
front magnetic bearing rotor magnet rings mounted on the rotor shaft adjacent the impeller;
the motor rotor magnets being mounted on the rotor shaft adjacent the impeller front magnetic bearing rotor magnet rings; and
rear magnetic bearing rotor magnet rings mounted on the rotor shaft adjacent the motor rotor magnets;

wherein a front end portion of the rotor shaft extending forward of the impeller defines a front journal of the front partial arc journal bearing, and wherein a rear end portion of the rotor shaft extending rearward of the rear magnetic bearing rotor magnet rings defines a rear journal of the rear partial arc journal bearing.

32. The blood pump recited in claim 18, wherein the bushings are aligned with each other radially about the pump axis.

33. The blood pump recited in claim 18, wherein the centers of the partial arcs of the bushings are positioned on the pump axis.

34. The blood pump recited in claim 18, wherein the front partial arc journal bearing is positioned in the pump inlet and the rear partial arc journal bearing is positioned in the pump outlet.

35. A blood pump comprising:
a pump housing having a pump inlet and a pump outlet spaced apart along a longitudinally extending central pump axis;
a rotating assembly comprising an impeller; and
partial arc journal bearings that support the rotating assembly for rotation in the housing, wherein the rotating assembly is rotatable relative to the housing to pump blood from the pump inlet to the pump outlet, wherein each of the partial arc journal bearings comprises a cylindrical journal component of the rotating assembly and a bushing component fixed to the housing, the bushing having a partial arc configuration extending partially around the circumference of the journal, and wherein the bushings are aligned with each other radially about the pump axis.

36. The blood pump recited in claim 35, wherein:
the pump further comprises a stator assembly supported in the housing, the stator assembly comprising motor stator windings, a front magnetic bearing stator, and a rear magnetic bearing stator; and
the rotating assembly comprises motor rotor magnets that align axially with the motor stator windings, a front magnetic bearing rotor that aligns with the front magnetic bearing stator, and a rear magnetic bearing rotor that aligns with the rear magnetic bearing stator.

37. The blood pump recited in claim 36, wherein the front and rear magnetic bearing stators each comprise one or more magnetic rings configured to produce a region of increased magnetic flux density on a bushing side of the pump, and wherein the front and rear magnetic bearing rotors comprise one or more magnetic rings in a full ring configuration, wherein the front and rear magnetic bearing stators are configured to act on the front and rear magnetic bearing rotors to exert a net radial force on the rotating assembly that pulls the rotating assembly into the partial arc journal bearings.

38. The blood pump recited in claim 37, wherein the front and rear magnetic bearing stators comprise permanent magnet partial rings.

39. The blood pump recited in claim 38, wherein the permanent magnet partial rings are positioned on the bushing side of the pump.

40. The blood pump recited in claim 36, wherein the stator assembly comprises:
a stator housing;
a motor stator supported in the stator housing;
front magnetic bearing stator magnetic rings mounted on the stator housing in front of the motor stator; and
rear magnetic bearing stator magnetic rings mounted on the stator housing to the rear of the motor stator.

41. The blood pump recited in claim 35, wherein the pump housing comprises an inner housing and an outer housing between which an axially extending primary flow channel is defined, the blood pump being configured to pump blood through the primary flow channel.

42. The blood pump recited in claim 41, wherein the primary flow channel is annular and extends outside the stator assembly and the rotating assembly.

43. The blood pump recited in claim 41, further comprising helical flow straightening vanes that extend between the inner and outer housings in the primary flow channel.

44. The blood pump recited in claim 35, further comprising magnetic rings that help constrain axial movement of the rotating assembly relative to the housing, the magnetic rings being configured to exert a net radial force on the rotating assembly that pulls the journals into their associated bushings.

45. The blood pump recited in claim 44, wherein the partial arc journal bearings are configured such that the partial arcs of the bushings are radially aligned with the magnetic rings.

46. The blood pump recited in claim 35, wherein the magnetic rings maintain the axial position of the rotating assembly in the housing.

47. The blood pump recited in claim 35, wherein the magnetic rings comprise one or more magnets configured to produce a region of increased magnetic flux density that pulls the rotating assembly into the partial arc journal bearings.

48. The blood pump recited in claim 35, wherein the rotating assembly comprises:
a rotor shaft;
an impeller mounted toward a front end portion of the rotor shaft;
front magnetic bearing rotor magnet rings mounted on the rotor shaft adjacent the impeller;
the motor rotor magnets being mounted on the rotor shaft adjacent the impeller front magnetic bearing rotor magnet rings; and
rear magnetic bearing rotor magnet rings mounted on the rotor shaft adjacent the motor rotor magnets;
wherein a front end portion of the rotor shaft extending forward of the impeller defines a front journal of the front partial arc journal bearing, and wherein a rear end portion of the rotor shaft extending rearward of the rear magnetic bearing rotor magnet rings defines a rear journal of the rear partial arc journal bearing.

49. The blood pump recited in claim 35, wherein the bushings extend radially 90-300 degrees around the circumference of their associated journals.

50. The blood pump recited in claim 35, wherein the centers of the partial arcs of the bushings are positioned on the pump axis.

51. The blood pump recited in claim 35, wherein the front partial arc journal bearing is positioned in the pump inlet and the rear partial arc journal bearing is positioned in the pump outlet.

52. A blood pump comprising:
a pump housing having a pump inlet and a pump outlet spaced apart along a longitudinally extending central pump axis;
a rotating assembly comprising an impeller; and
partial arc journal bearings that support the rotating assembly for rotation in the housing, wherein the rotating assembly is rotatable relative to the housing to pump blood from the pump inlet to the pump outlet, wherein each of the partial arc journal bearings comprises a cylindrical journal component of the rotating assembly and a bushing component fixed to the housing, the bushing having a partial arc configuration extending partially around the circumference of the journal, wherein the centers of the partial arcs of the bushings are positioned on the pump axis.

53. The blood pump recited in claim 52, wherein:
the pump further comprises a stator assembly supported in the housing, the stator assembly comprising motor stator windings, a front magnetic bearing stator, and a rear magnetic bearing stator; and
the rotating assembly comprises motor rotor magnets that align axially with the motor stator windings, a front magnetic bearing rotor that aligns with the front magnetic bearing stator, and a rear magnetic bearing rotor that aligns with the rear magnetic bearing stator.

54. The blood pump recited in claim 53, wherein the front and rear magnetic bearing stators each comprise one or more magnetic rings configured to produce a region of increased magnetic flux density on a bushing side of the pump, and wherein the front and rear magnetic bearing rotors comprise one or more magnetic rings in a full ring configuration, wherein the front and rear magnetic bearing stators are configured to act on the front and rear magnetic bearing rotors to exert a net radial force on the rotating assembly that pulls the rotating assembly into the partial arc journal bearings.

55. The blood pump recited in claim 54, wherein the front and rear magnetic bearing stators comprise permanent magnet partial rings.

56. The blood pump recited in claim 55, wherein the permanent magnet partial rings are positioned on the bushing side of the pump.

57. The blood pump recited in claim 53, wherein the stator assembly comprises:
a stator housing;
a motor stator supported in the stator housing;
front magnetic bearing stator magnetic rings mounted on the stator housing in front of the motor stator; and
rear magnetic bearing stator magnetic rings mounted on the stator housing to the rear of the motor stator.

58. The blood pump recited in claim 52, wherein the pump housing comprises an inner housing and an outer housing between which an axially extending primary flow channel is defined, the blood pump being configured to pump blood through the primary flow channel.

59. The blood pump recited in claim 58, wherein the primary flow channel is annular and extends outside the stator assembly and the rotating assembly.

60. The blood pump recited in claim 58, further comprising helical flow straightening vanes that extend between the inner and outer housings in the primary flow channel.

61. The blood pump recited in claim 52, wherein the magnetic rings maintain the axial position of the rotating assembly in the housing.

62. The blood pump recited in claim 52, wherein the magnetic rings comprise one or more magnets configured to produce a region of increased magnetic flux density that pulls the rotating assembly into the partial arc journal bearings.

63. The blood pump recited in claim 52, wherein the rotating assembly comprises:
a rotor shaft;
an impeller mounted toward a front end portion of the rotor shaft;
front magnetic bearing rotor magnet rings mounted on the rotor shaft adjacent the impeller;
the motor rotor magnets being mounted on the rotor shaft adjacent the impeller front magnetic bearing rotor magnet rings; and
rear magnetic bearing rotor magnet rings mounted on the rotor shaft adjacent the motor rotor magnets;
wherein a front end portion of the rotor shaft extending forward of the impeller defines a front journal of the front partial arc journal bearing, and wherein a rear end portion of the rotor shaft extending rearward of the rear magnetic bearing rotor magnet rings defines a rear journal of the rear partial arc journal bearing.

64. The blood pump recited in claim 52, wherein each of the partial arc journal bearings comprises a cylindrical journal component of the rotating assembly and a bushing component fixed to the housing, the bushing having a partial arc configuration extending partially around the circumference of the journal.

65. The blood pump recited in claim 52, further comprising magnetic rings that help constrain axial movement of the rotating assembly relative to the housing, the magnetic rings being configured to exert a net radial force on the rotating assembly that pulls the journals into their associated bushings.

66. The blood pump recited in claim 52, wherein the partial arc journal bearings are configured such that the partial arcs of the bushings are radially aligned with the magnetic rings.

67. The blood pump recited in claim 52, wherein the bushings extend radially 90-300 degrees around the circumference of their associated journals.

68. The blood pump recited in claim 52, wherein the bushings are aligned with each other radially about the pump axis.

69. The blood pump recited in claim 52, wherein the front partial arc journal bearing is positioned in the pump inlet and the rear partial arc journal bearing is positioned in the pump outlet.

* * * * *